US012366502B2

(12) United States Patent
Starynkevitch et al.

(10) Patent No.: US 12,366,502 B2
(45) Date of Patent: Jul. 22, 2025

(54) SYSTEM AND METHOD FOR DETERMINING A ROUNDED VALUE OF AN OPTICAL FEATURE OF AN OPHTHALMIC LENS ADAPTED TO PROVIDE A DIOPTRIC CORRECTION FOR IMPROVING THE VISION OF A SUBJECT

(71) Applicant: Essilor International, Charenton-le-Pont (FR)

(72) Inventors: Helene Starynkevitch, Charenton-le-Pont (FR); Adele Longo, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 188 days.

(21) Appl. No.: 18/005,221

(22) PCT Filed: Jul. 13, 2021

(86) PCT No.: PCT/EP2021/069488
§ 371 (c)(1),
(2) Date: Jan. 12, 2023

(87) PCT Pub. No.: WO2022/013231
PCT Pub. Date: Jan. 20, 2022

(65) Prior Publication Data
US 2023/0266198 A1    Aug. 24, 2023

(30) Foreign Application Priority Data
Jul. 15, 2020   (EP) .................................... 20305814

(51) Int. Cl.
*G01M 11/02*  (2006.01)
*A61B 3/028*  (2006.01)
*G16H 10/20*  (2018.01)

(52) U.S. Cl.
CPC ......... *G01M 11/0207* (2013.01); *A61B 3/028* (2013.01); *G16H 10/20* (2018.01)

(58) Field of Classification Search
CPC ......... A61B 3/028; A61B 3/032; A61B 3/066; A61B 3/08; A61B 3/036; G16H 10/20; G02C 7/027; G01M 11/0207
See application file for complete search history.

(56) References Cited

U.S. PATENT DOCUMENTS 5,148,205 A * 9/1992 Guilino .................. G02C 7/022
                                                        359/652
5,892,567 A    4/1999 Hosoi et al.
(Continued)

FOREIGN PATENT DOCUMENTS

CN    107847123 A    3/2018
CN    109475290 A    3/2019
(Continued)

OTHER PUBLICATIONS

International Search Report issued Sep. 21, 2021 is PCT/EP2021/069488 filed on Jul. 13, 2021, 4 pages.
(Continued)

*Primary Examiner* — Sang H Nguyen
(74) *Attorney, Agent, or Firm* — Oblon, McClelland, Maier & Neustadt, L.L.P.

(57) ABSTRACT

A system for determining a rounded value of an optical feature of an ophthalmic lens including determining a first test value and a first variation increment, performing a first trial of said subjective test wherein two first different optical situations are determined based on at least the first test value, determining a second test value based on the first test value, on the first variation increment and on the result of the first trial, performing a second trial of said subjective test wherein two second different optical situations are determined based on at least the second test value, determining an
(Continued)

intermediary value based on the result of the first trial and on the result of the second trial, and determining said rounded value by rounding said intermediary value to a reference value, said rounding modifying the dioptric correction of said ophthalmic lens by less than a predetermined basic dioptric value.

16 Claims, 7 Drawing Sheets

(56) References Cited

U.S. PATENT DOCUMENTS

| | | | |
|---|---|---|---|
| 11,409,131 B2 | 8/2022 | Marin et al. | |
| 2011/0228225 A1 | 9/2011 | Liang | |
| 2013/0107202 A1 | 5/2013 | Liang | |
| 2014/0368795 A1 | 12/2014 | Liang | |
| 2015/0185504 A1* | 7/2015 | Peloux | G02C 7/083 |
| | | | 351/159.39 |
| 2016/0120402 A1* | 5/2016 | Limon | A61B 3/0033 |
| | | | 351/239 |
| 2016/0242641 A1 | 8/2016 | Liang | |
| 2017/0261767 A1* | 9/2017 | Ohlendorf | G02C 7/081 |
| 2019/0261848 A1* | 8/2019 | Marin | A61B 3/028 |
| 2021/0106216 A1 | 4/2021 | Longo et al. | |

FOREIGN PATENT DOCUMENTS

| | | |
|---|---|---|
| CN | 110602977 | 12/2019 |
| DE | 197 28 186 A1 | 1/1998 |
| EP | 2018061207 | 5/2018 |
| WO | WO 2010/065475 A2 | 6/2010 |
| WO | WO 2019/099952 A1 | 5/2019 |

OTHER PUBLICATIONS

Revert et al. "An alternative clinical routine for subjective refraction based on power vectors with trial frames", Ophthalmic & Physiological Optics, The Journal of the College of Optometrists, vol. 37, 2017, pp. 24-32.

Office Action dated Mar. 28, 2025, issued in counterpart CN Application No. 202180060994.4, with English Translation, citing documents No. 15-17. (18 pages).

* cited by examiner

SYSTEM AND METHOD FOR DETERMINING A ROUNDED VALUE OF AN OPTICAL FEATURE OF AN OPHTHALMIC LENS ADAPTED TO PROVIDE A DIOPTRIC CORRECTION FOR IMPROVING THE VISION OF A SUBJECT

TECHNICAL FIELD OF THE INVENTION

The invention relates to a system and a method for determining a rounded value of an optical feature of an ophthalmic lens adapted to provide a dioptric correction for improving the vision of a subject.

BACKGROUND INFORMATION AND PRIOR ART

Manufacturing an ophthalmic lens adapted to improve the vision of a subject requires the determination of a value of an optical feature of said ophthalmic lens adapted to the subject. To determine such a value of said optical feature, the eye-care professional usually performs a subjective test on the subject thanks to appropriate optic devices. Numerous documents describe devices and methods for determining this value of the optical feature of the ophthalmic lens. This optical feature may include for example sphere power, cylinder power or cylinder axis.

Typically, said subjective test comprises several steps, hereafter called trials, during each of which the subject is required to compare two different optical situations taking into account a test value of an optical feature. A subjective test therefore corresponds to a sequence of trials. Depending on the feedback of the subject on this comparison, designated in the following as the answer of the subject, the eye-care professional increments the test value and, in the next trial of the subjective test, present the subject with two new different optical situations based on the incremented test value. This process is repeated until a specific answer or combination of answers is given by the subject. The prescribed value of the optical feature is then usually determined as a function of the test value used in the last trial of said subjective test.

In order to determine accurate value of the optical feature, new devices allow the eye-care professional to use small increments between successive trials of a subjective tests. For example, phoropters using variable lenses allow using increments smaller than 0.2 D.

In this context, the determined values of the optical features are precise but do not take into account the standard values of optical features of ophthalmic lenses available on the market.

Ophthalmic lenses are indeed not commercially available for any value of their optical features. Only a predetermined set of values, called hereafter "standard values" of each optical feature is available.

Moreover, devices and methods using small increments between successive trials of a subjective test usually lead to extended examination times and to a risk that the subjects does not perceive any difference between two successive trials of the subjective test. Thus, the eye-care professional may need to shorten the test because the subject under test is getting impatient, under stress, experiencing eye fatigue or having a lack of attention.

Therefore, there is also a need for a device and a method wherein the increment would allow on the one hand the subject to clearly understand the subjective test and on the other hand to reduce examination time, while avoiding exceeding the correct values of the optical features.

SUMMARY OF THE INVENTION

Therefore one object of the invention is to provide a system for determining a rounded value of an optical feature of at least an ophthalmic lens adapted to provide a dioptric correction for improving the vision of a subject, said system comprising an optical device for performing a subjective test comprising assessing the visual performance of the subject placed in two different optical situations and a computer comprising one or more processors programmed to implement the steps of:

a) determining a first test value of the optical feature and a first variation increment of the optical feature, b) using said optical device, performing a first trial of said subjective test wherein two first different optical situations are determined based on at least the first test value, c) determining a second test value of the optical feature based on the first test value, on the first variation increment and on the result of the first trial performed in step b), d) using said optical device, performing a second trial of said subjective test wherein two second different optical situations are determined based on at least the second test value, e) determining an intermediary value of the optical feature based on the result of the first trial performed in step b) and on the result of the second trial performed in in step d), f) determining said rounded value of the optical feature by rounding said intermediary value to a reference value, said rounding modifying the dioptric correction of said ophthalmic lens by less than a predetermined basic dioptric value.

By "modifying the dioptric correction of said ophthalmic lens by less than a predetermined basic dioptric value", it is meant that between an ophthalmic lens that would present a value of an optical feature equal to the intermediary value and the ophthalmic lens actually presenting the rounded value of the optical feature, the dioptric corrections provided by these two ophthalmic lenses would differ by less than the basic dioptric value. The "dioptric correction" of the lens corresponds to the overall optical power of the lens that is obtained with the optical features of the lens, such as sphere power, cylinder power and axis.

The reference value refers for example to a standard predetermined value. The reference value is for example comprised in the predetermined set of standard values of the corresponding optical feature that is available to be ordered or manufactured.

So, thanks to the system according to the invention, the rounded value of the optical feature may correspond to a standard value of the optical feature. This allows obtaining a value of the looked-for optical feature that is compatible with the standard values currently in place for manufacturing the lens.

These standard values of the predetermined set are preferably discrete values regularly spaced apart. The basic dioptric value is then representative of this regular spacing. It is equal, in practice to the difference between two successive standard values of the set of standard values.

In the example described here, standard values are equal to multiples of the basic dioptric value. By multiple, it is meant that the standard value is a product of the basic dioptric value by an integer. For example, sphere power is often prescribed and manufactured as a multiple of 0.25 D.

In this context, the processor may be programmed to round, in step e), said intermediary value to the closest or the second closest multiple of said predetermined basic dioptric value, when said intermediary value of the optical feature is different from a multiple value of said predetermined basic dioptric value.

The system according to the invention may also take into account personal features of the subject. This provides adaptability to the system. Here, a personal feature is, in a general manner, any feature related to the physical or optical condition of the subject.

The processor therefore may be further programmed to, in step a), determine the first variation increment based on at least a first personal feature of the subject.

Adapting the variation increment, here the first variation increment but also any successive variation increments, to the subject allows for example reducing the number of trials of a subjective test to perform before determining the intermediary value of the optical feature.

When the difference between the two different optical situations is based on the variation increment, adapting the variation increment to the subject also prevents uncertain answers when the subject perceives no differences between the two optical situations.

For example, for a sphere power determination test, the variation increment may be increased with the age of the subject. It can be equal to 0.30 D for a 20 year old subject with a good vision, 0.55 D for a 50 year old subject with myopia and 1.30 D for an 85 year old patient presenting several pathologies.

The processor can also be further programmed to, in step f), round said intermediary value according to a rounding method depending on at least a second personal feature of the subject or depending on the type of subjective test performed. The second personal feature can be the same than the first personal feature or another personal feature different from the first personal feature.

This also allows, for example, selecting between the closest or the second closest multiple of said predetermined basic dioptric value as a function of the age of the subject. For example, the intermediary value can be rounded to the lower value, among the closest or the second closest multiple, for a young subject to prevent his eyes to get used to the correction. The intermediary value can be rounded to the higher value, among the closest or the second closest multiple, for an old subject to make sure the correction sufficiently improves his vision.

As another example, for a subject with myopia, the intermediary value is preferentially rounded to the lower value, among the closest or the second closest multiple, whereas for a subject with hypermetropia, the intermediary value is preferentially rounded to the lower value, among the closest or the second closest multiple.

For a subject needing a correction principally for far vision, for example for a professional driver, the intermediary value is preferentially rounded to the lower value, whereas for a subject needing a correction principally for near vision, the intermediary value is preferentially rounded to the higher value, among the closest or the second closest multiple.

The intermediary value can also be rounded so that the difference between the rounded value and a value obtained from a previous optical equipment of the subject is a minimum difference.

Other advantageous and non limiting features of the system according to the invention are:
the first personal feature comprises at least one of the following data relative to the subject: age, type of ametropia, visual acuity, complains regarding his visual performance or current vison correction equipment, historical data including current correction of the subject, pathologies, visual needs or activities, chosen spectacle frame, chosen ophthalmic lens, optical feature of the eye of the subject;
the second personal feature comprises at least one of the following data relative to the subject: age, type of ametropia, visual acuity, complains regarding his visual performance or current vison correction equipment, historical data including current correction of the subject, pathologies, visual needs or activities, chosen spectacle frame, chosen ophthalmic lens, optical feature of the eye of the subject;
the processor is further programmed to determine, in step b), the two first different optical situations based on the first variation increment;
said subject is placed in said two different optical situations during said subjective test by achieving at least one of the following:
 displaying targets placed in a red and green environment,
 adding, in front of the eye of the subject a cross cylinder in two different positions,
 placing, in front of the eye of the subject, two lenses of different spheres,
 displaying two targets of different size,
 placing different lenses in front of the right and left eye of the subject;
the optical feature comprises at least one of following:
 sphere power of said ophthalmic lens,
 cylinder power of said ophthalmic lens,
 cylinder axis of said ophthalmic lens,
 difference in sphere power between two ophthalmic lenses placed in front of the right and left eyes;
the processor is further programmed to implement the steps of:
 g) determining a current test value and a current variation increment based on the result of a preceding trial and on a preceding test value corresponding to said preceding trial,
 h) performing a current trial of said subjective test, comprising assessing the visual performance of the subject placed in two current different optical situations determined based on at least the current test value,
 i) modifying the current test value based on the of the current trial and on the current variation increment, and modifying the current variation increment based on the result of the current trial,
and,
optionally, repeat steps h) and i),
and the processor is programmed to determine, in step e), said intermediary value based on the current test value;
the processor is further programmed to determine, in step g), and/or to modify, in step i), the current variation increment based on a degree of certainty of the result of said preceding trial test performed;
the current variation increment is smaller than said predetermined basic dioptric value;
the processor is further programmed to modify, in step i), the current variation increment by decreasing its value;

the processor is further programmed perform said step e), when:
the current test value is successively increased and decreased or decreased and increased in the last two successive trials, or
the second test value is higher than the first test value and the current test value determined in step g) is smaller than the second test value, or
the second test value is smaller than the first test value and the current test value determined in step g) is higher than the second test value;
the processor is further programmed perform said step e), when:
during a final trial the subject assesses the two final different optical situations to provide an equivalent visual performance, and
during a preceding trial performed before said final trial, the subject assessed one of the two different preceding optical situations, to provide a better quality of vision than the other preceding optical situation.

The invention also relates to a method for determining a rounded value of an optical feature of an ophthalmic lens adapted to provide a dioptric correction for improving the vision of a subject, which can be executed by the system described above and comprises steps a) to f).

DETAILED DESCRIPTION OF EXAMPLE(S)

The following description, enriched with joint drawings that should be taken as non limitative examples, will help understand the invention and figure out how it can be realized.

Figure 1:
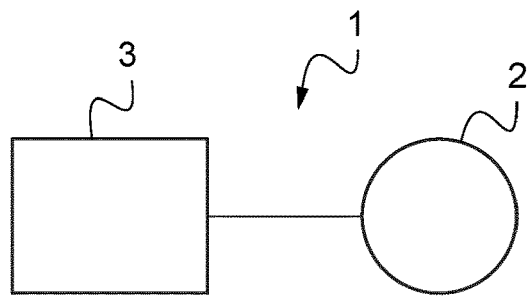
FIG. 1 is a schematic representation of a system according to the invention.
Figure 7:
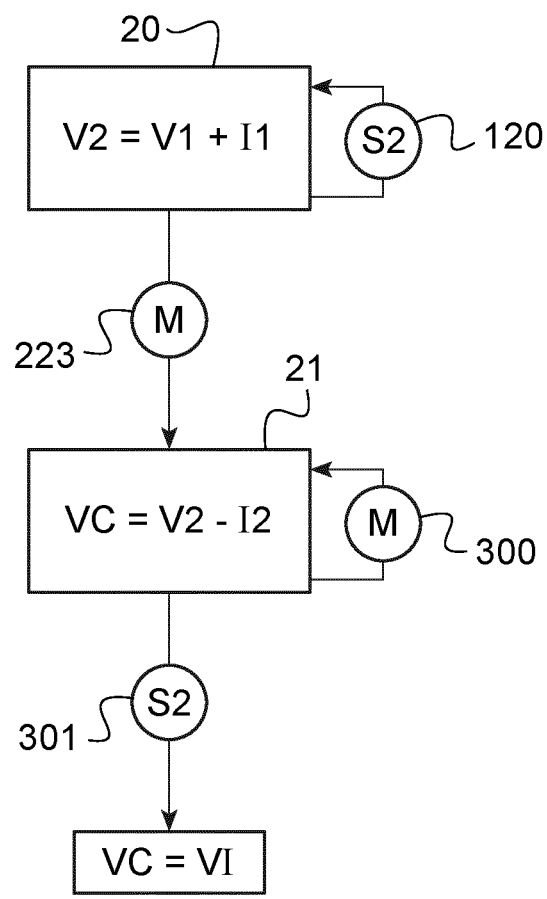
Figure 8:
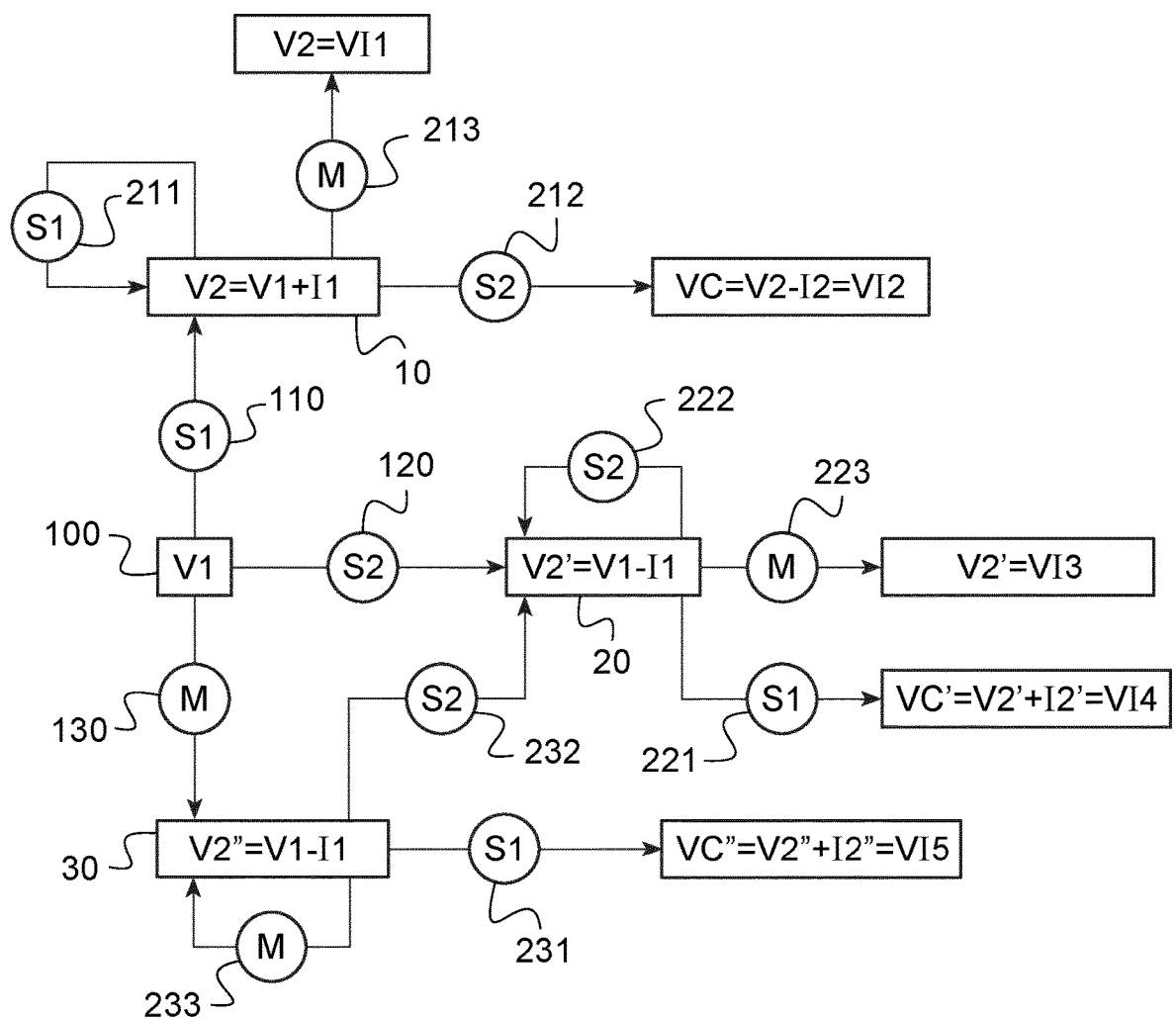

FIG. 7 is a schematic representation of a fourth decision tree of a fourth sequence of trials of a fourth subjective test aiming at determining a sphere power value of the ophthalmic lens with relaxation of the accommodation of the subject, programmed in a fourth embodiment of the system of FIG. 1, wherein each trials of said fourth subjective test comprises displaying two targets of different size;

FIG. 8 is a schematic representation of a fifth decision tree of a fifth sequence of trials of a fifth subjective test aiming at determining a bi-ocular balance value of two ophthalmic lenses adapted to the eyes of a subject, programmed in a fifth embodiment of the system of FIG. 1, wherein each trial of said fifth subjective test comprises displaying placing different lenses in front of the right and left eye of the subject.

FIG. 1 represents a system 1, according to the invention, comprising an optical device 2 and a computer 3.

The optical device 2 is adapted to perform trials of a subjective test by providing the subject with two different optical situations.

As will be described in more details later, different subjective tests may be performed to determine optical features of the ophthalmic lens. Each subjective test is associated with specific optical situations that are provided to the subject. These optical situations, and therefore, the optical device adapted to provide them, may have different characteristics depending on the optical feature determined through the corresponding subjective test.

The optical feature can comprise a dioptric optical feature, i.e. an optical feature measured in diopters, or an orientation, i.e. an optical feature representing an angle, for example measured in degrees.

Here, the optical feature comprises for example one or more of the following: a sphere power, a cylinder power, a cylinder axis, a difference in sphere between right and left eyes.

To this end, the subjective test may comprise one or more of the following:
duochrome test to determine sphere power,
cross cylinder test to determine cylinder power and/or axis,
acuity test without accommodation relaxation to determine sphere power,
acuity test with accommodation relaxation to determine sphere power,
bi-ocular balance test.

Detailed examples will be provided later.

The corresponding optical device may therefore comprise optical means for:
placing, in front of the eye of the subject, a trial lens having an optical feature equal to a test value and displaying, here simultaneously, targets comprising a sign placed on a red or green environment,
displaying a target of having multiple elements and adding, in front of the eye of the subject a cross cylinder placed successively in two different positions depending on a cylinder axis test value,
placing successively, in front of the eye of the subject, two trial lenses having an optical feature equal to two different test values (different spheres) and displaying a target,
placing, in front of the eye of the subject, a trial lens having an optical feature equal to a test value and displaying two targets of different size,
placing simultaneously different trial lenses in front of the right and left eye of the subject and displaying a target for each eye.

In practice, the optical device 2 comprises for example a phoropter equipped with a trial lens having a variable optical feature.

As a variant, the optical device 2 may also comprise a set of trial lenses having different values for said optical feature.

Additionally, the optical device 2 comprises a device for displaying said target. The device for displaying said target may be any kind of displaying device, such as a screen. It may comprise an active digital screen such as a liquid crystal display, or a passive screen and a projection device.

Depending on the subjective test performed, said optical device 2 may also comprise cross cylinders.

The optical device 2 is described in more details with the first to fifth subjective tests illustrated in FIGS. 3, 4, 6, 7 and 8.

The computer 3 comprises for example one or more processor and one or more memory. Here, instructions, in particular to implement steps illustrated in FIG. 2 for determining a rounded value of an optical feature of an ophthalmic lens adapted to provide a dioptric correction for improving the vision of a subject, are stored in said one or more memory. Said one or more processor is then programmed to execute these steps.

Here, the computer 3 comprises a user screen for displaying information to an eye-care professional and an inputting device allowing the eye-care professional to interact with the computer. The inputting device may comprise a keyboard, mouse, touch screen, voice controlled means, the user screen itself when the latest is touchable, or any other known inputting means.

Figure 5:
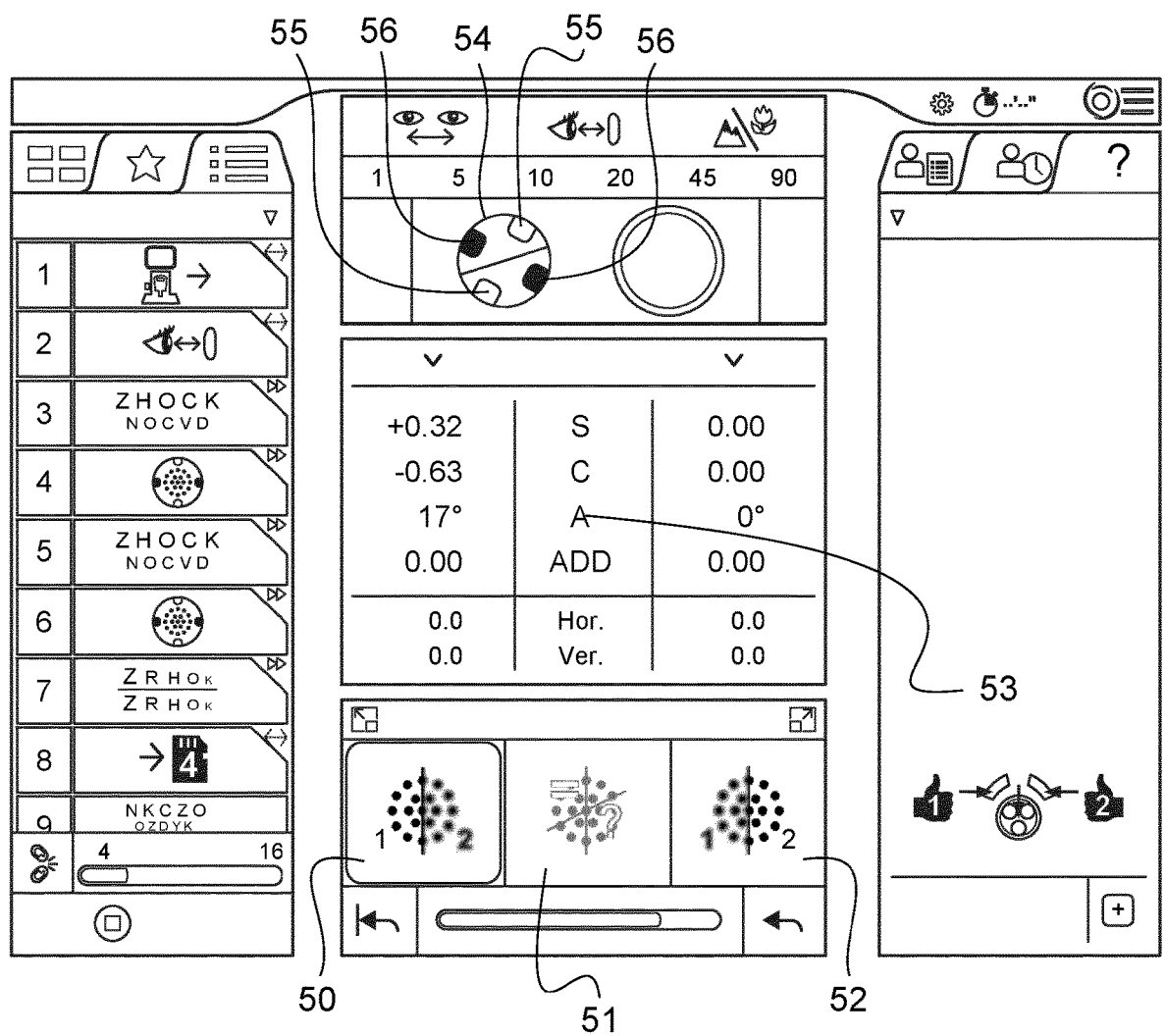
FIG. 5 is an illustration of a user interface that the eye-care professional can use to conduct the determination of the rounded value of the optical feature.

An example of a user interface displayed on the user screen is shown in FIG. 5, which is described in more detailed with a second subjective test performed according to the method of the invention.

Here, the computer 3 comprises a communication device allowing the computer to connect to and command the optical device 2, for example to command the target screen of the optical device 2.

Figure 2:
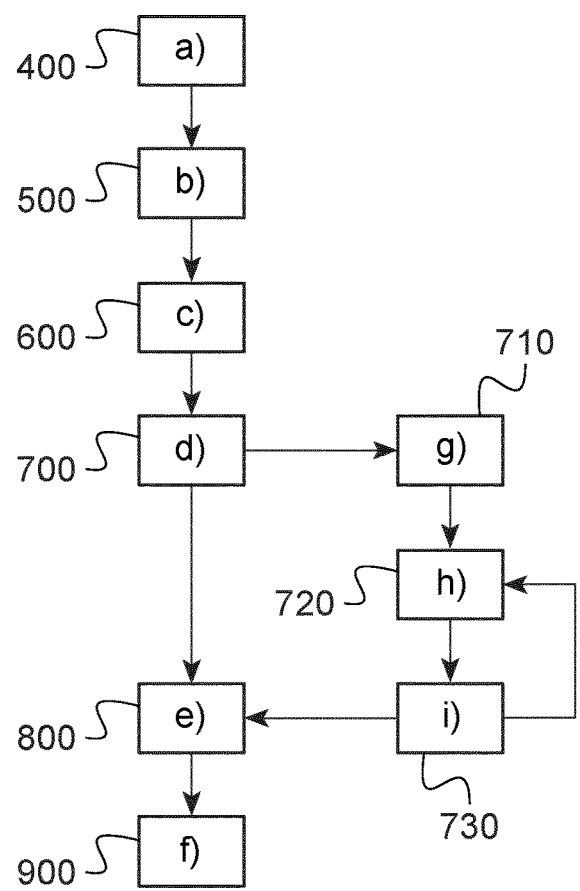
FIG. 2 is a bloc diagram schematically showing the steps of the method for determining a rounded value of an optical feature of an ophthalmic lens adapted to provide a dioptric correction for improving the vision of a subject according to the invention, implemented by the system of FIG. 1.

FIG. 2 illustrated a method, implemented by the system 1, for determining a rounded value of an optical feature of an ophthalmic lens adapted to provide a dioptric correction for improving the vision of a subject.

In all embodiments of the invention, the method comprises the steps of:
- a) determining (400) a first test value of the optical feature and a first variation increment of the optical feature,
- b) using said optical device, performing (500) a first trial of a subjective test wherein two first different optical situations are determined based on at least the first test value,
- c) determining (600) a second test value of the optical feature based on the first test value, on the first variation increment and on the result of the first trial performed in step b),
- d) using said optical device, performing (700) a second trial of said subjective test wherein two second different optical situations are determined based on at least the second test value,
- e) determining (800) an intermediary value of the optical feature based on the result of the first trial performed in step b) and on the result of the second trial performed in step d),
- f) determining (900) said rounded value of the optical feature by rounding said intermediary value to a reference value, said rounding modifying the dioptric correction of said ophthalmic lens by less than a predetermined basic dioptric value.

The method is not limited to performing two trials of a subjective test. Indeed, the number of trials of said subjective test required to determine the intermediary value may be greater than two.

The processor may be further programmed to implement the steps of:
- g) determining (710) a current test value and a current variation increment based on the result of a preceding trial and on a preceding test value corresponding to said preceding trial,
- h) performing (720) a current trial of said subjective test, comprising assessing the visual performance of the subject placed in two current different optical situations determined based on at least the current test value,
- i) modifying (730) the current test value based on the result of the current trial and on the current variation increment, and modifying the current variation increment based on the result of the current trial, and, optionally, repeat steps h) and i), and to determine, in step e), said intermediary value based on the current test value.

In the following, the wording "current" refers to any trial of the subjective test after the first and the second trials and to the test value and variation increment associated to this current trial. In step i), modifying the current test value and the current variation increment means that those two parameters are incremented, updated or adjusted.

A preceding trial designates, in a general manner, any trial having occurred before the current trial. It may be the first, second or any other trial having occurred before the current trial. In practice, the current test value and, optionally, the current variation increment, are determined based on the test value and/or variation increment of the immediately preceding trial. It may be the second or any other trial having occurred before the current trial. However, given the successive nature of the trials, the current test value and current variation increment nonetheless depend on the test values and variation increment of all the preceding trials.

Step a)

In the first step a), a first test value V1 of the optical feature is determined.

The first test value may be determined based on historical data of the subject, on the results of previous subjective tests or on an objective measurement.

The first test value may for example be obtained from a previous optical equipment of the subject. This determination of the first test value is particularly interesting when the subject is already wearing ophthalmic lenses and when he wishes to adapt his current correction.

The first test value may also be determined based on the results of other previous subjective tests or on the results of preceding trials of the same subjective test. The preceding trials of the subjective test may have been performed immediately before step a), by the same eye-care professional carrying the method according to the invention. The other previous subjective test may have been performed by the same eye-care professional or by another eye-care professional, immediately before the current subjective test or in the past.

In this case, the determination of the first test value may take into account a degree of certainty of the result of said subjective test.

When the optical feature is a dioptric optical feature, the first test value can be determined thanks to an objective refraction test. The objective refraction test can be performed with a retinoscopy device or an auto-refractor which may be comprised in the optical device 2. The objective refraction test may be performed immediately before step a), by the same eye-care professional performing step a). It may also be performed by another eye-care professional or may have been performed in the past.

The first test value can also be determined by the eye-care professional based on a personal feature of the subject or on a combination of personal features.

Said personal feature of the subject may comprise any of the first or second personal features described hereafter.

In addition, in the first step a), a first variation increment I1 is determined.

The first variation increment I1 may be a predetermined value depending on the subjective test performed in step b).

It may also be determined based on the results of other previous subjective tests or on the results of preceding trials of the same subjective test.

In this case, the determination of the first variation increment may take into account a degree of certainty of the result of said subjective test.

In an embodiment, the processor is programmed to, in step a), determine the first variation increment I1 based on at least a first personal feature of the subject.

The first personal feature comprises for example at least one of the following data relative to the subject: age, type of ametropia, visual acuity, complains regarding his visual performance or current vison correction equipment, historical data including current correction of the subject, pathologies, visual needs or activities, chosen spectacle frame, chosen ophthalmic lens, optical feature of the eye of the subject. An optical feature of the eye of the subject may for example comprise: aberration of the eye, opacity of the eye, an optical feature of the eye measured objectively. The first personal feature may also comprise a magnitude linked to the sensitivity of the subject, that is to say to his ability to perceive a variation of a dioptric correction of a lens.

For example, when determining a sphere power such as in the first, third and fourth subjective test, for a subject with a low visual acuity (for example 3/10), the first variation increment is preferentially superior to 1 D, whereas for a subject with a high visual acuity (for example 12/10), the first variation increment is preferentially inferior to 0.5 D or 0.3 D.

As described later, the first variation increment I1 is used in step c) to determine the second test value V2 used in the second trial of the subjective test.

Preferentially, the first variation increment I1 is superior to the basic dioptric value. The first variation increment I1 is for example superior to 0.3 D or to 10 degrees. This allows converging rapidly to a test value representative of the correction needed by the subject. In other words, this allows reducing the number of trials required to determine the rounded value of the optical feature. The first variation increment I1 used in the first trial of the subjective test is also preferentially higher than increment values used in further trials of the subjective test, as described in more details hereafter.

Step b)

Two first different optical situations are determined based on at least the first test value V1.

After determining the first test value V1, in a step b), a first trial of the subjective test is performed.

To this end, two first different optical situations S1, S2 are determined based at least on the first test value V1 and are presented to the subject thanks to the optical device 2. During the first trial of the subjective test, the subject is asked to gaze at one or more targets through one or more trial lenses which characteristics, for example their sphere power or their orientation, are based on the first test value 1. Here, the targets are displayed on the target screen of the optical device 2.

The two first different optical situations S1, S2 may also take into account the first variation increment I1. This is for example the case of the third subjective test described later.

During the first trial of the subjective test, the subject is asked to compare the two first optical situations S1, S2, i.e., here, to assess which one of the two first optical situations S1, S2 provides higher visual performance according to the subject's perception. To obtain this information, depending on the subjective test performed, the eye-care professional may for example ask, "in which situation do you better see the target" or "which target do you better see".

It is possible that in none of the first optical situations S1, S2, the subject can clearly distinguish the target. In the case, the subject assesses in which one he better distinguishes the target.

A result of a trial of the subjective test consists in an answer of the subject given by the subject to assess which one of the two first optical situations S1, S2 provides a better quality of vision, for example as an answer to one of the above referenced questions. In this way, here, a result may consist in one of three different answers:

i) first answer: the subject indicates that a given optical situation S1 among the two optical situations S1, S2 provides better quality of vision, in other words better visual performance, than the other optical situation S2;

ii) second answer: the subject indicates the other optical situation S2 of the two optical situations S1, S2 to provide better quality of vision in other words better visual performance, than the optical situation S1 previously considered;

iii) third answer: the subject indicates the two optical situations S1, S2 to provide an equivalent visual performance or that he cannot choose a better optical situation among the two optical situations. This last indication illustrates an "I don't know" answer.

As a variant, the answers could be defined as followed: the first answer may be the indication that none of the two optical situations provides a good quality of vision, the second answer may be the indication that both optical situations provide a good quality of vision and the third answer may be the indication that one out of the two optical situations provides a good quality of vision.

In the following, the two optical situations will be designated by the same reference S1 and S2 for each trial although they vary from one trial to the next. Optical situations referenced by S1 in each trial are called hereafter optical situation of the first type, whereas optical situations referenced by S2 in each trial are called hereafter optical situation of the second type. As will be explained in detail later, optical situations of the first type have common features or common difference relative to the optical situations of the second type.

For example, in the duochrome test, optical situations S1 corresponding the green targets will be of the first type, whereas optical situations S2 corresponding the red targets will be of the second type. In the acuity test, optical situations S1 corresponding the target of lower acuity or to the lens with lower sphere power will be of the first type, whereas optical situations S2 corresponding the target of higher acuity or to the lens with higher sphere power will be of the second type.

The optical situations referenced S1 or S2 correspond to each other.

In practice, the eye-care professional enters the result of the trial of the subjective test in the computer 3 thanks to the inputting device. For example, on the user interface illustrated in FIG. 5, the eye-care professional selects, for example by a click, the left button 50 when the result of the first trial is the first answer. He selects the right button 52 when the result is the second answer. He selects the central button 51 when the result is the third answer.

The trials of the subjective tests and the dependency of the two optical situations on the test value and possibly on the variation increment are described in more details in the first to fifth subjective tests illustrated in FIGS. 3, 4, 6, 7 and 8.

Step c)

In a step c), a second test value V2 of the optical feature is determined. The second test value V2 is in particular determined based on the first test value V1, on the first variation increment I1 and on the result of the first trial of the subjective test performed in step b).

The determination of the second test value may take into account a degree of certainty of the result of said first trial.

Here, the second test value V2 is for example calculated as the sum or the difference between the first test value V1 and the first variation increment I1, that is to say, by adding or subtracting the first variation increment I1 to the first test value V1. As showed for example in FIG. 3, the second test value V2 can thus be calculated according to the following equation $V2=V1\pm I1$, where the sign ± indicates a + or − sign.

The second test value V2 may also be calculated as a weighted sum or difference between the first test value V1 and the first variation increment I1. As showed for example in FIG. 6, the second test value V2 can thus be calculated according to the following equation $V2=V1\pm C\times I1$, where C is a real positive coefficient, for example comprised between 0.1 and 5, preferably comprised between 0.5 and 2.

The result of the first trial determines whether the second test value V2 is higher or lower than the first test value V1, and therefore, if the first variation increment I1 is added or subtracted to the first test value V1.

Depending on the subjective test, obtaining the first answer or the second answer as a result of the first trial respectively induces the second test value V2 to be superior or inferior to the first test value V1.

Depending on the subjective test, obtaining the third answer as a result of the first trial induces the second test value V2 to be superior or inferior to the first test value V1. In other words, in the first trial of the subjective test, the third answer is processed either as a first or as a second answer.

Indeed, obtaining the third answer as the result of the first trial may be regarded as a misunderstanding of the subjective test by the subject. So, the second test value V2 is also determined higher or lower than the first test value V1 after the third answer. Depending on the subjective test, as long as the third answer is successively obtained as the result of successive trials, the test value is increased or decreased from one trial to the next.

In a preferred embodiment, a second variation increment I2 is moreover determined, for example based on the result of the first trial and on the first variation increment I1. Preferentially, the second variation increment I2 is smaller than the first variation increment I1: it is decreased. Also preferentially, the second variation increment I2 may be lower than the basic dioptric value.

As a variant, the second variation increment is bigger than the basic dioptric value. This authorizes to perform a quick subjective test.

The determination of the second variation increment may take into account a degree of certainty of the result of said first trial.

Step d)

In step d), two second different optical situations, one S1 of the first and one S2 of second type, are determined based on the second test value V2, and a second trial of said subjective test is performed using these second different optical situations.

The second trial of said subjective test is similar to the first trial. The second trial of the subjective test only differs from the first trial in that the two different optical situations S1, S2 provided to the subject depend on the second test value V2 and not on the first test value V1.

In the same way as the first trial, the two second different optical situations S1, S2 can also take into account the second variation increment I2.

During the second trial of the subjective test, the subject is asked to compare the two second optical situations, to assess which one of the two second optical situations provides a better visual performance. The result of the second trial is also a first, second or third answer given by the subject.

The first answer corresponds to the subject indicating that the second optical situation S1 of the first type among the two second optical situations provides better visual performance, the second answer corresponds to the subject indicating the second optical situation S2 of second type provides better visual performance, and the third answer corresponds to the subject indicating that the two second optical situations S1, S2 provide an equivalent visual performance or that he cannot choose a better optical situation among the two second optical situations.

Step g)

The first and second trial described above may actually correspond to the two initial trials performed when beginning the sequence of trials of the subjective test. They also may correspond to any two successive trials among said sequence of trials.

More generally, during each trial of the subjective test, the subject is asked to compare the two current optical situations, one S1 of the first type and one S2 of the second type, to assess which one of the two current optical situations provides a better visual performance.

Ulterior steps of the method according to the invention are therefore described hereafter in a more general manner.

In a step g), a current test value VC is determined. The current test value VC is determined by taking into account the preceding test values and the results of the preceding trials of the subjective test. Here, the current test value VC is also determined by taking into account the preceding variation increment.

The previous test value, previous variation increment and previous trial correspond in the following to the immediately preceding test value, variation increment and trial. It may be the second test value, second variation increment and second trial.

As all the test values are determined taking into account the preceding test values and preceding trial results, the current test value is in particular determined taking into account the second test value V2, the result of the second trial of the subjective test performed in step d) and the second variation increment I2.

The current test value VC is for example calculated as the sum or the difference between the previous test value VP and the previous variation increment IP. The current test value V2 can thus be calculated according to the following equation VC=VP±IP.

The current test value VC may also be calculated as a weighted sum or difference between the previous test value VP and the previous variation increment IP. The current test value VC can thus be calculated according to the following equation VC=VP±C×IP, where C is a real positive coefficient, for example comprised between 0.5 and 2.

The result of the previous trial of subjective test determines whether the current test value VC is higher or lower than the previous test value VP.

In practice, depending on the subjective test, the first answer (the subject indicates the optical situation S1 of the first type) and the second answer (the subjection indicates the optical situation S2 of the second type) respectively induces a current test value VC higher or lower to the previous test value VP.

Depending on the subjective test, and on the result of the preceding trials, the third answer induces either calculating a current test value VC or determining directly the intermediary value VI. More precisely, the third answer induces determining directly the intermediary value VI, when the result of a preceding trial is the first or the second answer.

In addition, a current variation increment IC can be determined, for example based on the result of the previous subjective test and on the previous variation increment.

Here, the processor may be further programmed to determine the current variation increment IC and/or the current test value based on a degree of certainty of the result of a preceding trial performed, preferably, of the previous trial.

In a general manner, in order to take into account the degree of certainty of the subject, certitude data indicative of the degree of certainty of the subject upon giving the first, second or third answer is collected and recorded in said one or more memory and associated to the corresponding answer to each trial of the subjective test. Here, the degree of certainty is determined as in document US 2019261848. Said certitude data may thus be based on a measurement of the time duration the subject takes to give his answer while looking at the target, or on other measurement by sensors, such as a pressure sensor associated with a button that the subject uses to record his answer. Any mean known from the man skilled in the art may be used.

For example, when the result of a current trial is a first or a second answer but is unsure, that is to say, when the degree of certainty is below a predetermined threshold, the variation increment is preferentially decreased. Indeed, this means that the current test value is close to the correction needed by the subject.

When the degree of certainty is high, a first or a second answer might be processed as a third answer.

Step h)

Two current different optical situations, one S1 of the first type and one S2 of the second type, are determined based on at least the current test value VC.

A current trial of the subjective test is performed by presenting to the subject the two current optical situations.

The current trial is similar to the first and second trials.

In the same way as the first and second trials, the two current different optical situations S1, S2 can also be determined based on the second current increment IC.

During the current trial of the subjective test, the subject is asked to compare the two current optical situations, to assess which one of the two current optical situations provides a better quality of vision. The result of the current trial is also a first, second or third answer given by the subject.

Step i)

After step h), in the step i), the current test value VC is modified to determine an updated test value VCup based on the result of the current trial of the subjective test and on the current variation increment IC.

Here, the updated current test value VCup after modification is for example calculated as the sum or the difference between the current test value VC and the current variation increment IC. The updated current test value VCup can thus be calculated according to the following equation VCup=VC±IC.

In practice, the first answer and the second answer respectively induce an increase or a decrease of the current test value VC, that is to say, an updated current test value lower or higher than the current test value.

Depending on the subjective test, and on the result of the first subjective and second trial, the third answer induces either an increase or a decrease of the current test value VC, that is to say, the determination of an updated current test value higher or lower than the current test value, or determining directly the intermediary value VI. More precisely, the third answer induces determining directly the intermediary value VI, when the result of a preceding trial test (i.e. the first, the second or a current trial) is the first or the second answer.

After modifying the current test value, i.e. after calculating the updated current test value VCup, the current variation increment IC is modified based on the result of the current trial.

The updated test value VCup is taken into account in the next current trial as the current test value.

In the same way as the determination of the current test value, the processor may be further programmed to modify the current variation increment based on a degree of certainty of the result of said preceding trial.

Here, preferentially after few repetitions of steps h) and i), for example 1 to 4 repetitions, the current variation increment is smaller than said predetermined basic dioptric value.

In this way, the current test value VC may have a precision smaller than the basic dioptric value. So, the current test value can be accurately representative of the correction needed by the subject. Therefore, the intermediary value VI determined in step e) is also accurately representative of the correction needed by the subject.

As a variant, the current variation increment may be bigger than said predetermined basic dioptric value. This authorizes to perform a quick subjective test.

In an embodiment, the processor is further programmed to modify, in step i), the current variation increment by decreasing its value.

This also allows determining a very precise current test value, i.e. with a precision higher than the basic dioptric value.

When the following first or second stop conditions occur, the processor stops repeating steps h) and i) or does not perform them at all. In other words, when those stop conditions occur, the processor immediately performs step e).

The first stop condition occurs when:
during a final trial of the subjective test, in other words during the trial last performed, the subject assesses the two final different optical situations to provide an equivalent visual performance, i.e. the result of the final trial is the third answer, and during a preceding trial of the subjective test performed before said final trial, the subject assessed one of the two different preceding optical situations to provide a better quality of vision than the other preceding optical situation, i.e. the result of the final trial is the first or the second answer.

The final trial of the subjective test is here the second trial or any ulterior current trial. The preceding trial can be any trial performed before the final trial. Here, the preceding trial is more specifically the previous trial performed immediately before the final trial.

When the first stop condition occurs, it means the test value tested during the final trial is accurately representative of the correction needed by the subject.

The second stop condition occurs when:
the current test value has been successively increased and decreased or decreased and increased in the last two successive trials, or
the second test value is higher than the first test value and the current test value determined in step g) is smaller than the second test value, or
the second test value is smaller than the first test value and the current test value determined in step g) is higher than the second test value.

For example, when three successive trials called a first, a second and a current trial have been performed, the second stop condition can occur when:
the updated current test value is higher than the current test value and the current test value is lower than the second test value, or
the updated current test value is lower than the current test value and the current test value is higher than the second test value The second stop condition allows determining the intermediary value VI faster (i.e. by performing fewer trials) than waiting only for the first condition to occur. In practice, it means that the intermediary value VI can be determined even if no third answer has been given, i.e. even if the correction needed by the patient has not been tested as a test value during a trial.

In this case, the determined intermediary value VI is comprised between the two last test values. For example, here, the intermediary value VI is determined as the mean between the two last test values. This allows determining an intermediary value IC accurately representative of the correction needed by the subject.

Step e)

In step e), the intermediary value VI of the optical feature is determined based on the results of the first and second trials tests performed in step b) and d).

As described above, depending on the results of the first and second trials, step e) may be performed immediately after step d). In this case, only the first and the second trials are performed.

For example, this is the case when the first stop condition occurs after the second trials.

In this case, the intermediary value VI is equal to the second test value V2.

As described above, depending on the results of the first and second trials, step e) may be performed immediately after step g). In this case, only the first and the second trials are performed.

For example, this is the case when the second stop condition occurs after the determination of the current test value in step g), i.e. when the second test value is higher than the first test value and the current test value determined in step g) is smaller than the second test value, or when the second test value is smaller than the first test value and the current test value determined in step g) is higher than the second test value, the intermediary value VI can be calculated as the mean between the current test value and the second test value.

When further trials are implemented, a current test value VC and a current variation increment are determined and the determination of the intermediary value VI is also based on the current test value VC and on the current variation increment VI.

When further trials are implemented, the intermediary value VI can for example be equal to the last test value or calculated as the mean between the two last test values.

For example, when the current test value is successively increased and decreased or decreased and increased in the last two successive trials, i.e. in the last two implementations of steps h) and i), the intermediary value VI can be calculated as the mean between the two last current test values.

As an example, when the result of a current trial is the third answer, the intermediary value VI can be determined as equal to the current test value.

Step f)

After determining the intermediary value VI, the rounded value of the optical feature is determined by rounding the intermediary value VI to a reference value.

The rounding is performed so that the dioptric correction of the ophthalmic lens is modified by less than a predetermined basic dioptric value.

When the optical feature is a dioptric optical feature, this means that the difference between the rounded value and the intermediary value is smaller than the basic dioptric value.

When the optical feature is a cylinder axis, this means that difference in orientation between the rounded value and the intermediary value is perceived by the subject as a change in cylinder power smaller than the basic dioptric value. Indeed, in a well known manner in the field of cylindrical lenses, an orientation change of the cylinder axis induces a dioptric change of the cylinder power. Consequently, a modification of the cylinder axis can be transcribed in a modification of the cylinder power.

So, when the optical feature is a cylinder axis, modifying the dioptric correction of the ophthalmic lens by less than a predetermined basic dioptric value means that the dioptric change of the cylinder power induced by the change in cylinder axis is smaller than the predetermined basic dioptric value.

For example, when the cylinder power is inferior to 1.5 D the axis may be rounded to a multiple of 5 degrees. Whereas when the cylinder power is superior to 1.5 D, rounding to a multiple of 5 degrees can induce a cylinder power change superior to 0.25 D. Thus, when the cylinder power is superior to 1.5 D, the intermediary value is preferentially rounded to a multiple of 2 degrees.

The dioptric change observed also depends on the cylinder power of the test lens itself.

The basic dioptric value can be determined by the eyecare professional based on the precision of the prescription that he aims to deliver. The basic dioptric value is for example 0.25 D.

As described above, the reference value is here a standard value used in manufacture of ophthalmic lenses. Here, when the optical feature is a dioptric optical feature, the reference value is more precisely defined as a multiple of the basic dioptric value. When the optical feature is a cylinder axis, the reference value is defined as a multiple of a given angle, for example five degrees.

Here, when the optical feature is a dioptric optical feature, the one or more processor of said optical device 2 is more precisely programmed to round said intermediary value to the closest or the second closest multiple of the predetermined basic dioptric value, when the intermediary value of the optical feature is different from a multiple value of the predetermined basic dioptric value.

For example, when the intermediary value VI determined, in step e), is 0.87 D, and when the basic dioptric value is 0.25 D, the closest and second closest multiples of 0.25 D 0.75 D and 1 D. The intermediary value VI can therefore be rounded to 0.75 D or 1 D.

In the same way, when the optical feature is the cylinder axis, the one or more processor of said optical device 2 is more precisely programmed to round said intermediary value to the closest or the second closest multiple of said given angle, when the intermediary value of the optical feature is different from a multiple value of said given angle.

For example, when the intermediary value VI determined, in step e), is 17 degrees, and when the basic dioptric value is 5 degrees, the multiples of 5 degrees closest and second closest to 17 degrees D are 15 degrees and 20 degrees: the intermediary value VI can be rounded to 15 degrees or 20 degrees.

Here, the processor is further programmed to round the intermediary value VI according to a rounding method depending on at least a second personal feature of the subject or depending on the type of subjective test performed.

The second personal feature comprises for example at least one of the following data relative to the subject: age, type of ametropia, visual acuity, complains regarding his visual performance or current vison correction equipment, historical data including current correction of the subject, pathologies, visual needs or activities, chosen spectacle frame, chosen ophthalmic lens, optical feature of the eye of the subject.

For example, for an subject whose age is over a threshold value, the intermediary value VI is preferentially rounded to the higher value among the closest and second closest values, whereas for a subject whose age in under said threshold the intermediary value VI is preferentially rounded to the lower value among the closest and second closest values.

Following the example wherein the intermediary value VI determined, in step e), is 0.87 D, for an old subject, the intermediary value VI is preferentially rounded to the higher value, i.e. 1 D, whereas for a young subject the intermediary value VI is preferentially rounded to the lower value, i.e. 0.75 D.

According to other examples, the intermediary value can be rounded to the lower value, among the closest or the second closest multiple, for a subject having a visual acuity over a given threshold value and/or no complains regarding his visual performance or current vision equipment and/or no specific pathologies, low visual needs, not activity requiring a improved visual acuity. The intermediary value can be rounded to the higher value, among the closest or the second closest multiple, for a subject having a visual acuity lower than a threshold, and/or complains regarding his visual performance or current vision equipment, and/or specific pathologies, and/or high visual needs, and/or having activities requiring a improved visual acuity.

Five subjective tests, each comprising a sequence of trials are now described in reference to FIGS. 3 to 8. A sequence of trials comprises all the steps a) to f) of the method according to the invention and thus allows determining one rounded value of an optical feature. In the following, when a test value is determined as the sum between the previous test value and the previous variation increment, it is said to be increased. Inversely, when a test value is determined as the difference between the previous test value and the previous variation increment, it is said to be decreased.

Here, the first answer corresponds, in most of the examples described, to the indication that the optical situation S1 of the first type gives better visual performance than the other, the second answer corresponds to the indication that the optical situation S2 of the second type gives better visual performance than the other, and the third answer corresponds to the indication that both optical situation S1, S2 of the first and second type gives equivalent visual performance.

As a variant, described for example in relation with the fourth subjective test, the first answer may correspond the indication that none of the two optical situations provides a good quality of vision, the second answer may correspond to the indication that both optical situations provide a good quality of vision and the third indication correspond be the indication that one out of the two optical situations provides a good quality of vision.

First and second answer will be represented on the figures by the reference of the corresponding optical situations S1 and S2. The third answer will be represented on the figures by the reference M.

Common references are used in the FIGS. 3, 4, 6, 7 and 8 for the first, second and third answer.

First Subjective Test

Figure 3:
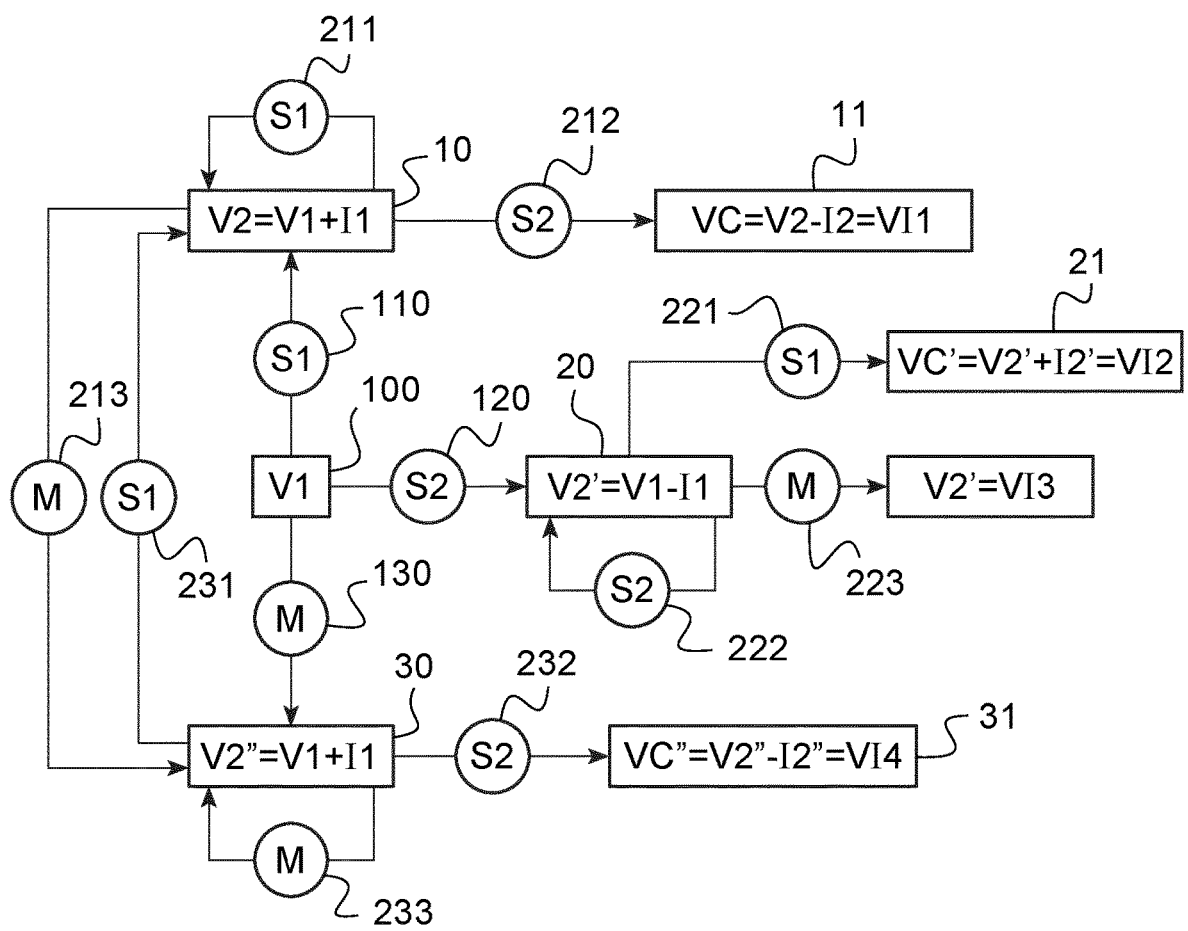
FIG. 3 is a schematic representation of a first decision tree of a first sequence of trials of a first subjective test aiming at determining a sphere power value of the ophthalmic lens, programmed in a first embodiment of the system of FIG. 1, wherein each trial of said first subjective test comprises displaying targets placed in a red and green environment.
Figure 4:
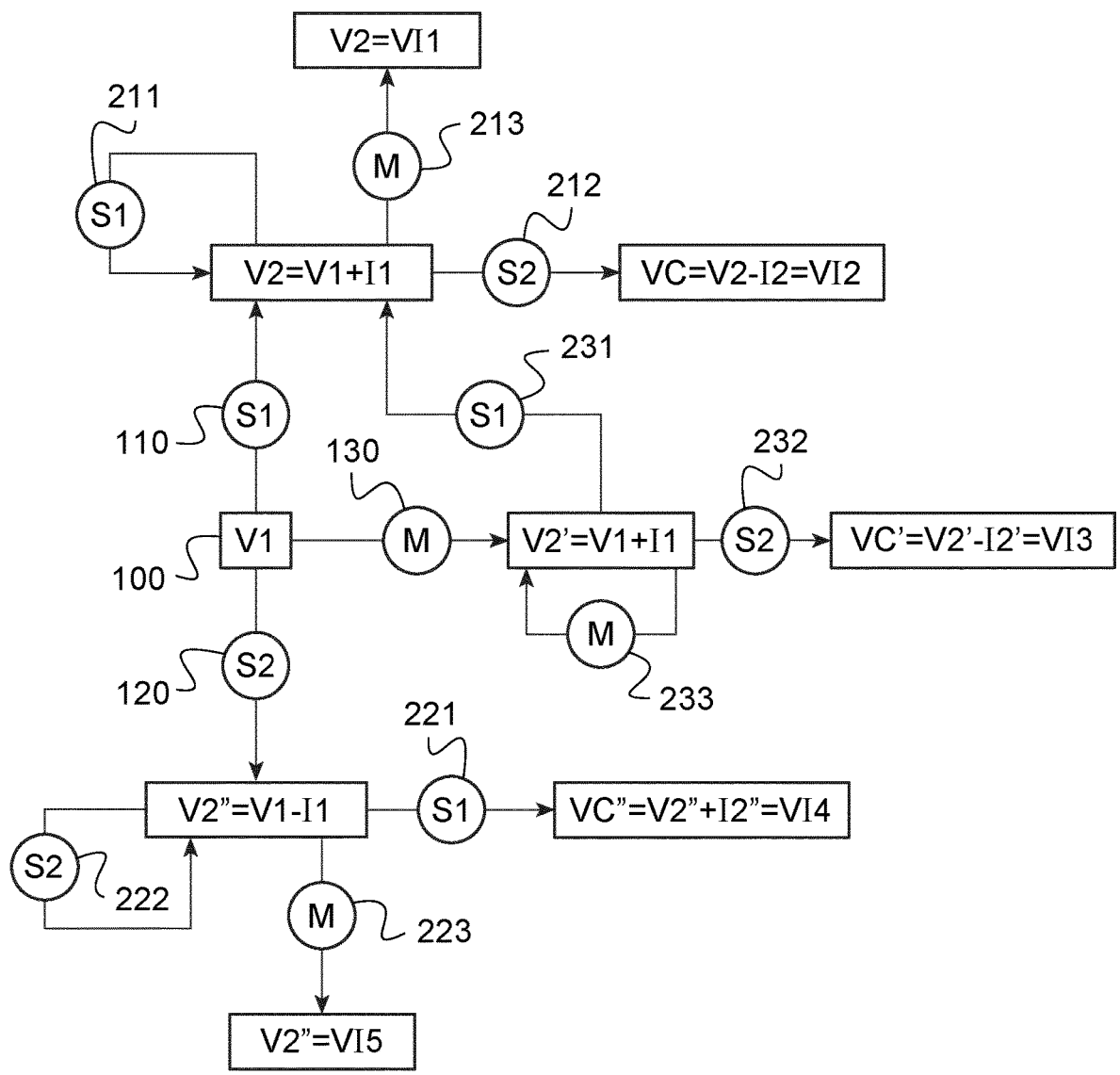
FIG. 4 is a schematic representation of a second decision tree of a second sequence of trials of a second subjective test aiming at determining a cylinder axis value of the ophthalmic lens, programmed in a second embodiment of the system of FIG. 1, wherein each trial of said second subjective test comprises adding, in front of the eye of the subject, a cross cylinder in two different positions.

The decision tree of a sequence of a first subjective test is illustrated in FIG. 3.

In this first subjective test, the optical feature of the ophthalmic lens is a sphere power.

Each trial comprises displaying two targets, each comprising a sign placed in a red and green environment and providing the subject with a trial lens having a trial sphere power value.

This subjective test is often known as the "duochrome test". Here, this subjective test is a monocular test. The rounded value is determined for one eye. The sequence can be performed a second time or in parallel for the other eye. In this last case, the first subjective test may therefore be a binocular test.

The targets are displayed on the target screen of the optical device 2.

In the optical situation S1 of the first type, a first target of said two targets comprises a sign displayed in a uniform green background. Said sign comprises for example an optotype or a geometrical shape.

In the optical situation S2 of the second type, a second target of said two targets comprises a sign displayed in a uniform red background. Said sign comprises for example an optotype or a geometrical shape. The second sign may be identical to the first sign.

During each trial, the subject is asked to look at the two targets through the trial lens having a trial sphere power value equal to the test value, and to identify with which target the sign appears sharper.

In step a), referenced 100 in FIG. 3, the first test value can for example be determined as the current correction of the subject or based on an objective or subjective measurement.

For the first trial, the trial sphere power value of the trial lens is equal to the first test value V1.

If the subject sees the sign sharper on the green background than on the red background, the result of the first trial is the first answer 110. Optically, this means that trial sphere power value of the trial lens is not sufficient to provide an appropriate correction for the eye of the subject tested. It is therefore increased in the next trial. In step d), referenced 10 in FIG. 3, the second test value V2 is then determined as the sum of the first test value V1 and the first variation increment I1.

If the subject sees the sign sharper on the red background than on the green background, the result of the first trial is the second answer 120. Optically, this means that sphere power of the trial lens is too strong to provide an appropriate correction for the eye of the subject tested. It is therefore decreased in the next trial. In step d), referenced 20 in FIG. 3, the second test value V2 is then determined as the difference between the first test value V1 and the first variation increment I1.

More generally, when the result of a trial is a first answer 110, 221, 211, 231, the test value is increased and when the result of a trial is the second answer 120, 222, 212, 232, the test value is decreased.

If the subject sees the sign as equally sharp on the green and on the red background, the result of the first trial is the third answer 130. Optically, this means that sphere power of the trial lens is appropriate.

But, as described above, obtaining the third answer as a result of the first trial is regarded as a misunderstanding of the test by the subject. Here, in this case, the second test value V2 is also determined, in step d) referenced 30, as the sum of the first test value V1 and the first variation increment I1, i.e. as if the result of the first trial is the first answer.

As long as the result of the successive trials is the third answer 233, the test value is determined as the sum of the previous test value and the previous variation increment, i.e. is increased.

Here, the intermediary value VI, and so the rounded value, is looked for as the lower sphere power, in diopter, giving equally sharp sign in the two optical situation S1, S2. Consequently, obtaining the second answer (sign clearer on the red background) is mandatory before determining the intermediary value. Indeed, it is the only answer that makes sure that the trial sphere power value is lower than the appropriate value for visual correction of the subject. This also allows avoiding the accommodation of the subject which can bias the determination of the intermediary value.

This is why, all the branches of the decision tree represented in FIG. 3 that lead to the determination of the intermediary value VI comprise, at one point, a second answer 212, 120, 232.

The intermediary value VI1 is for example determined when the results of two successive trials are a first answer 110, 211, 231 followed by a second answer 212. In this case, the intermediary value VI1 is equal to the current test value VC which is determined, in step g) or i) referenced 11 in FIG. 3, as the difference between the previous test value V2 and the previous variation increment I2, where the previous variation increment I2 is equal to half its immediately preceding variation increment I1. The current test value VC is thus the mean between the two immediately preceding test values V2, V1. This case corresponds to the second stop condition.

The intermediary value VI2 may also be determined when the results of two successive trials are a second answer 120, 222 followed by a first answer 221. In this case, the intermediary value VI2 is equal to the current test value VC' which is determined, in step g) or i) referenced 21 in FIG. 3, as the sum between the previous test value V2' and the previous variation increment I2', where the previous variation increment I2' is half its immediately preceding variation increment I1. This case also corresponds to the second stop condition.

The intermediary value VI3 may also be determined when the results of two successive trials are a second answer 120, 222 followed by a third answer 223. In this case, the intermediary value VI3 is equal to the previous test value V2' determined in step c), g) or i). This case corresponds to the first stop condition.

Finally, the intermediary value VI4 can also be determined when the results of two successive trials are a third answer 130, 233, 213 followed by a second answer 232. In this case, the intermediary value VI4 is equal to the current test value VC" which is determined, in step g) or i) referenced 31 in FIG. 3, as the difference between the previous test value V2" and the previous variation increment I2" where the previous variation increment I2" is equal to its immediately preceding variation increment I1.

Preferentially, between the first trial and the last trial of the sequence, the variation increment is decreased. Preferentially, it is decreased from one trial to the next. For example, the first variation increment V1 is equal to 1 D and the second variation increment V2 is equal to 0.3 D.

In another example, the current variation increment is calculated as the value of the variation increment of a preceding trial, preferably of the previous trial, multiplied by a coefficient strictly lower then 1. Subsequently, the current variation increment preferentially becomes even lower than the basic dioptric value. The basic dioptric value is for example 0.25 D.

In this first sequence, in step f), the rounded value is determined by rounding the intermediary value to the closest or second closest multiple of the basic dioptric value. As described above, the rounding method can depend on a personal feature of the subject.

Second Subjective Test

The decision tree of a second subjective test is illustrated in FIG. 3.

This second subjective test is often known as the "cross cylinders test". It implies placing, in front of the eye of the subject, a cross cylinder in two different positions, i.e., here, in two different orientations. This subjective test is a monocular test. The rounded value is determined for one eye. The sequence can be performed a second time for the other eye.

In this example of the second subjective test, the optical feature is the cylinder axis. However, a similar subjective test with similar decision tree may be used to determine the cylinder power.

During each trial, the subject is asked to look at a target, for example displayed on the target screen of the optical device 2, through a trial lens which is known as "Jackson Cross Cylinder" and referred to here as the cross cylinder.

In the optical situation S1 of the first type, the cross cylinder is positioned in a first orientation.

In the optical situation S2 of the second type, the cross cylinder is positioned in a second orientation. Here, the second orientation is the result of a rotation by 90 degrees, with respect to the first orientation, around the axis of gaze of the eye so that the positive and the negative axis of the cross cylinder interchange.

Here, the positive axis is defined as the axis where the power of the cross cylinder is maximum, for example equal to +0.25 D or +0.5 D. The negative axis is defined as the axis where the power of the cross cylinder is minimum, for example equal to −0.25 D or −0.5 D.

When determining the cylinder axis, for each trial, the cross cylinder is positioned with respect to a trial cylinder axis value. Here, trial cylinder axis value is an angle in degrees with a predetermined direction, for example with the horizontal direction. In the optical situation S1 of the first type, the positive axis of the cross cylinder is oriented at 45 degrees from the trial cylinder axis value in an anticlockwise rotation and in the optical situation S2 of the second type, the positive axis of the cross cylinder is oriented at 45 degrees from the trial cylinder axis value in an clockwise rotation.

In the first trial, the trial cylinder axis value is equal to the first test value. In the second trial, the trial cylinder axis value is equal to the second test value. In a current trial, the trial cylinder axis value is equal to the current test value.

In FIG. 5, the trial cylinder axis value is represented by the letter A referenced 53. In FIG. 5, the trial cylinder axis value is equal to 17 degrees. The cross cylinder is represented by a circle referenced 54. The positive axis of the cross cylinder goes through two first poles 55 of the cross cylinder and the negative axis of the cross cylinder goes through two second poles 56 of the cross cylinder.

For the subject, in both optical situations S1, S2, the target seen through the cross cylinder appears unclear. During the subjective test, the eye-care professional may ask "in which situation is the target less blurred?".

So, in a general way, when the result of a trial is a first answer 110, 221, 211, 231, the test value is increased and when the result of a trial is the second answer 120, 222, 212, 232, the test value is decreased.

Unless the results of all preceding trials are a third answer, when the result is a third answer 213, 223, the intermediary value VI1, VI5 is then determined as equal to the last test value V2, V2". This corresponds to the first stop condition.

As in the first subjective test, obtaining the third answer as the result of the first trial is regarded as a misunderstanding of the subjective test by the subject. Here, in this case, the second test value V2' is determined as the sum of the first test value V1 and the first variation increment I1, i.e. as if the result of the first trial is the first answer.

As long as the result of the successive trials is the third answer 233, the test value is determined as the sum of the previous test value and the previous variation increment, i.e. is increased.

As in the first subjective test, the intermediary value VI2, VI4 is for example determined when the results of two successive trials are a first answer 110, 211, 231 followed by a second answer 212, or conversely, a second answer 120, 222 followed by a first answer 221. In this case, the intermediary value VI2, VI4 is equal to the current test value VC, VC" which is determined as the difference, or respectively the sum, between the previous test value V2, V2" and the previous variation increment I2, I2", where the previous variation increment I2, I2" is equal to half its immediately preceding variation increment I1. This case corresponds to the second stop condition.

Finally, the intermediary value VI3 can also be determined be determined when the results of two successive trials are a third answer 130, 233 followed by a second answer 232. In this case, the intermediary value VI3 is equal to the current test value VC' which is determined as the difference between the previous test value V2' and the previous variation increment I2', where the previous variation increment I2' is equal to its immediately preceding variation increment I1.

Preferentially, between the first trial and the last trial of the sequence, the variation increment is decreased. Preferentially, it is decreased from one trial to the next. For example, the first variation increment V1 is equal to 15 degrees and the second variation increment V2 is equal to 7 degrees. Subsequently, the current variation increment can become even lower than the basic dioptric value. The basic dioptric value is for example 5 degrees.

In this second sequence, in step f), the rounded value can be determined by rounding the intermediary value to the closest or second closest multiple of a given angle. Here, the intermediary value is preferentially rounded to the lower value among the closest or second closest multiple of a given angle. As described above, the rounding method can depend on a personal feature of the subject.

The cylinder power of the ophthalmic lens adapted to provide a dioptric correction for improving the vision of the subject may also be determined. The decision tree represented in FIG. 4 also applies to the determination of the cylinder power. When determining the cylinder power, the test value is a dioptric value. For each trial, the cross cylinder is oriented with respect to the cylinder axis previously determined. Here, in the optical situation S2 of the second type, the negative axis of the cross cylinder is aligned with the negative axis of the cylinder axis.

Here, the cross cylinder has a trial cylinder power value. In the first trial, the trial cylinder power value is equal to the first test value. In the second trial, the trial cylinder power value is equal to the second test value. In a current trial, the trial cylinder power value is equal to the current test value.

The first test value V1 is for example +0.25 D or −0.25 D.

When the subject sees the target sharper, that is to say, have a better visual performance, in the optical situation S1 of the first type, the test value, and so the cylinder power value, is increased. When the subject sees the target sharper, that is to say, have a better visual performance, in the optical situation S2 of the second type, the test value, and so the cylinder power of the cross cylinder, is decreased.

The first variation increment may depend on the difference between a cylinder power value obtained from a previous optical equipment of the subject and the first test value: the higher the difference is, the higher is the variation increment.

The cylinder axis and power is one way to represent a cylinder but other representations exist such as the J0, J45 representation as described in the document EP 2018061207. The decision tree represented in FIG. 4 also apply to the J0, J45 representation, for example by setting J45 to a determined value and looking for J0 and then setting J0 to the found value and looking for J45.

Third Subjective Test

Figure 6:
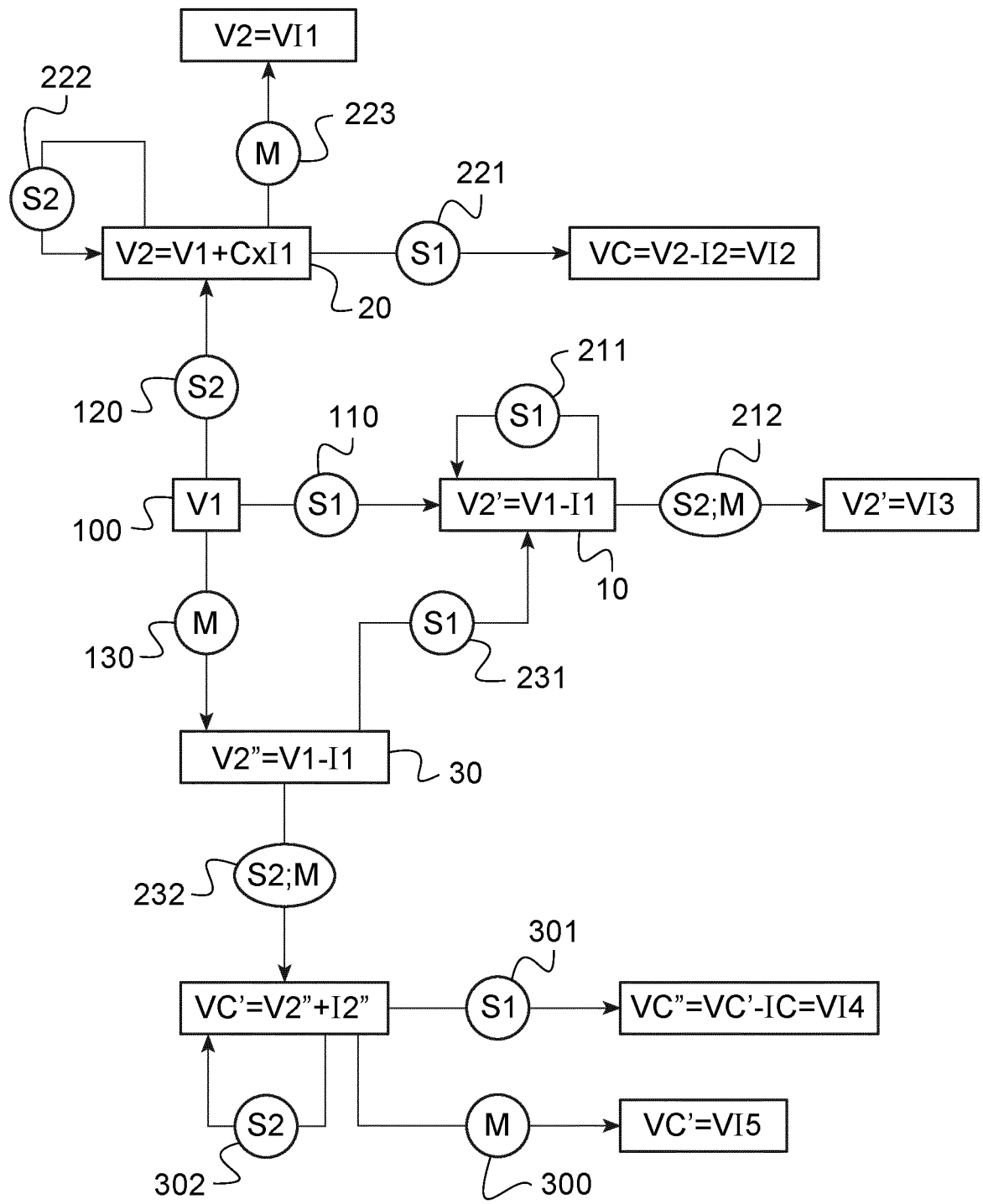
FIG. 6 is a schematic representation of a third decision tree of a third sequence of trials of a third subjective test aiming at determining a sphere power value of the ophthalmic lens, programmed in a third embodiment of the system of FIG. 1, wherein each trial of said third subjective test comprises placing, in front of the eye of the subject, two lenses of different spheres.

The decision tree of a third subjective test is illustrated in FIG. 6.

In this third subjective test, the optical feature determined is the sphere power. The test consists in placing, in front of the eye of the subject, two lenses of different spheres. This subjective test is a monocular test. The rounded value is determined for one eye. The subjective test can be performed a second time for the other eye.

In the optical situation S1 of the first type, the subject looks at a target, which is for example displayed on the target screen of the optical device 2, through a first trial lens. The first trial lens is characterized by a first trial sphere power value.

In the optical situation S2 of the second type, the subject looks at the same target through a second trial lens. The second trial lens is characterized by a second trial sphere power value which differs from the first trial sphere power value.

During each trial, the subject is asked to look successively at the target through the first and then the second trial lens.

Here, the intermediary value VI, and so the rounded value, is looked for as the lower sphere power, in diopter, giving equally sharp targets in the two optical situation S1, S2.

In step a), referenced 100 in FIG. 3, the first test value can for example be determined as the current correction of the subject or based on an objective measurement.

During the subjective test, the eye-care professional may ask "in which situation the letters appear clearer?".

For the first trial, the first trial sphere power value is equal to the first test value V1 minus the first variation increment. The second trial sphere power value is equal to the first test value.

More generally, for each trial, in the optical situation of the first type the first trial sphere power value is equal to the test value minus the variation increment and, in the optical situation of the second type the second trial sphere power value is equal to the test value.

For each trial, the first trial lens may be presented before or after the second trial lens.

If the subject sees the target sharper with the first trial lens than with the second trial lens, the result of the trial is the first answer. Optically, this means that sphere power of the second trial lens is too strong to provide an appropriate correction for the eye of the subject tested. When the result of the first trial is the first answer 110, in step d), referenced 10 in FIG. 6, the second test value V2' is then determined as difference between first test value V1 and the first variation increment I1, i.e. equal to the first trial sphere power value.

If the subject sees the target sharper with the second trial lens than with the first trial lens, the result of the first trial is the second answer. Optically, this means that sphere power of the second trial lens is not sufficient to provide an appropriate correction for the eye of the subject tested. When the result of the first trial is the second answer 120, in step d), referenced 20 in FIG. 3, the second test value is then determined as a weighted sum between the first test value V1 and the first variation increment I1. More precisely, the second test V2 is determined as the sum of the first test value V1 and the first variation increment I1 weighted by a coefficient C inferior to 1. For example, the weighting coefficient C is equal to 0.625. More generally, when the result of a trial is a first answer 110, 221, 211, 231, the test value is decreased and when the result of a trial is the second answer 120, 222, 212, 232, the test value is increased.

If the subject sees the targets as equally sharp in both optical situations S1, S2, the result of the first trial is the third answer 130.

But, as described above, obtaining the third answer as a result of the first trial is regarded as a misunderstanding of the test by the subject. Here, in this case, the second test value V2" is also determined, in step d) referenced 30, as the difference between the first test value V1 and the first variation increment I1, i.e. as if the result of the first trial is the first answer.

As long as the result of the successive test is the third answer 233, the test value is determined as the difference between the previous test value and the previous variation increment, i.e. is decreased.

Here, in order to facilitate the subject's understanding of the subjective test, i.e. helping the subject see a difference between the first optical situations S1, S2, the first variation increment I1 is high, for example superior to 0.35 D.

When the result of the first trial is the third answer 130 and when the result of the second trial is the second or the third answer 232, the current test value VC' is calculated as the sum between the second test value V2" and the second variation increment I2". In this case, the second variation increment I2" is superior to the first variation increment V1. For example, the second variation increment I2" is 1.625 time higher than the first variation increment I1.

Except from this specific branch of the decision tree, between the first trial and the last trial of the sequence, the variation increment is preferentially decreased.

When the result is a third answer 223, 212, 300, the second trial lens provides an appropriate correction for the eye of the subject tested. The intermediary value VI1, VI3, VI5 is then determined as equal to the current test value V2, V2', VC', i.e. to the second trial sphere power value. This corresponds to the first stop conditions. The only exception is the branch wherein the result of the first trial is the third answer 130 and the result of the second trial also the third answer 232.

As in the first and the second sequences, the intermediary value VI2, VI4 is for example determined when the results of two successive trials are a first answer 110, 211, 231 followed by a second answer 212, or conversely, a second answer 120, 222, 232, 302 followed by a first answer 221, 301. In this case, the intermediary value VI2, VI4 is equal to the current test value VC, VC".

Preferentially, between the first trial and the last trial of the sequence, the variation increment is decreased. Preferentially, it is decreased from one trial to the next. For example, the first variation increment V1 can be superior to 1 D and the second variation V2 inferior to 1 D. Subsequently, the current variation increment can become even lower than the basic dioptric value. The basic dioptric value is for example 0.25 D. In this third subjective test, in step f), the rounded value is determined by rounding the intermediary value to the closest or second closest multiple of the basic dioptric value. As described above, the rounding method may depend on a personal feature of the subject.

Fourth Subjective Test

The decision tree of a sequence of a fourth subjective test is illustrated in FIG. 7.

In this first subjective test, the optical feature of the ophthalmic lens is a sphere power.

Each trial comprises displaying two targets of different size and providing the subject with a trial lens having a trial sphere power value.

This subjective test is often known as the "fogging/defogging test". This subjective test is a monocular test. The rounded value is determined for one eye. The sequence can be performed a second time for the other eye.

In the optical situation S1 of the first type, the subject looks at a first target through the trial lens. The size of the first target, seen at the viewing distance of the subject, corresponds to a first acuity value.

In the optical situation two S2, the subject looks at a second target, smaller than the first target, through the same trial lens. The size of the second target, seen at the viewing distance of the subject, corresponds to a second acuity value.

During each trial, the subject is asked to look at the two targets through the trial lens having a trial sphere power value equal to the test value, and to identify with which target the sign appears sharper.

The two targets are for example lines of letters of an acuity chart. For example, for the first trial, the first target is a line at 4/10 and the second target a line at 8/10. The size of the first and second target may change from a trial to the next.

Here, during an optional initial part of the sequence (not represented in FIG. 7), the size of the first and second target may be increased until the subject can clearly read at least the first target.

Here, the result of a trial is the first answer when that the subject cannot clearly read the letters of none of the first and second target. The result of a trial is the second answer when the subject can clearly read the letters of both of the first and the second target. The result of a trial is the third answer when the subject can clearly read the letters of the first target but cannot clearly read the letters of the second target.

Here, in the first step a), the first test value can for example be determined as the current correction of the subject or based on an objective or subjective measurement, plus a determined dioptric value, for example superior to 1 D. This addition of a determined dioptric value corresponds to an initial fogging step. Indeed, in a first part of the sequence, a fogging allows relaxing the subject accommodation.

Then, as long as the subject can clearly read the second target, i.e. as long as the result of the successive trials is the second answer 130, the test value is increased. As represented in FIG. 7, when the result of the first trial is the second answer 120, the second test value V2 is calculated, in step c) referenced 20 in FIG. 7, as the sum between the first test value V1 and the first variation increment I1.

This increase of the test value corresponds to the first part of the sequence: the fogging step. Here, during the fogging step, the variation increment is preferably kept constant.

Then, at the moment when the subject can clearly read only the first target, i.e. when the result of the trial is the third answer, the test value is decreased. For example, in FIG. 7, when the result of the second trial is the third answer 223, the current test value VC is calculated, in step g) referenced 21, as the difference between the second test value V2 and the second variation increment I2.

This first decrease of the test value is the beginning of a second part of the sequence: the defogging step. Here, at the beginning of the second part of the sequence, the second target is set to a predetermined high acuity, for example a line corresponding to acuity 10/10.

Then, as long as the subject can clearly read only the first target, i.e. when the result of the successive trials is the third answer 300, the test value is decreased.

Here, during the defogging step, the variation increment preferably decreased from one trial to the next.

Then, at the moment when the subject can clearly read the second target, i.e. when the result of the trial is the second answer 301, the intermediary value VI is determined as the equal to the current test value VC. The intermediary value is here determined as equal to the current test value when a second answer is obtained with a second target corresponding to a predetermined wished for acuity.

In step f), the rounded value is determined by rounding the intermediary value to the closest or second closest multiple of the basic dioptric value. The basic dioptric value is for example 0.25 D. As described above, the rounding method can depend on a personal feature of the subject.

Fifth Subjective Test

The decision tree of a fifth subjective test is illustrated in FIG. 8.

In this fifth subjective test, the optical feature determined is a difference in sphere power between right and left eyes. The test consists in placing, in front of each eye of the subject, two lenses of different spheres.

This subjective test is a binocular test. The rounded value is determined for both eyes. In the optical situation S1 of the first type, the subject looks with his left eye at a target, which is for example displayed on the target screen of the optical device 2, through a left trial lens. The left trial lens is characterized by a left trial sphere power value.

In the optical situation S2 of the second type, the subject looks with his right eye at the same target through a right trial lens. The right trial lens is characterized by a right trial sphere power value which differs from the left trial sphere power value.

During each trial, the subject is asked to look successively at the target with his left eye through the left trial lens and then with his right eye through the right trial lens. A mask can be placed in front of one eye to allow the subject to look at the target only with the other eye.

Here, the intermediary value VI, and so the rounded value, is looked for as the difference between the left trial sphere power value and the right trial sphere power value giving the targets seen equally sharp with both eyes.

In step a), referenced 100 in FIG. 3, the first test value can for example be determined as the difference in sphere power between right and left eye based on the current correction of the subject or based on two objective monocular measurements, one for the right eye and one for the second eye.

During the subjective test, the eye-care professional may ask "in which situation does the letters appear clearer?".

For the first trial, the left trial sphere power value is equal to sphere power previously determined in a monocular test for the left plus a determined dioptric value, here 0.5 D, and the right trial sphere power value is equal to sphere power previously determined in a monocular test for the right eye plus the determined dioptric value.

If the subject sees the target sharper with the left trial lens, i.e. with the left eye, than with the right trial lens, the result of the trial is the first answer. When the result of the first trial is the first answer 110, in step d), referenced 10 in FIG. 8, the second test value V2 is then determined as the sum between first test value V1 and the first variation increment I1. This means that the difference between the left trial sphere power value and the right trial sphere power value is increased for the second trial.

If the subject sees the target sharper with the right trial lens, i.e. with the right eye, than with the left trial lens, the result of the trial is the second answer. When the result of the first trial is the second answer 120, in step d), referenced 20 in FIG. 8, the second test value V2' is then determined as the difference between first test value V1 and the first variation increment I1. This means that the difference between the left trial sphere power value and the right trial sphere power value is decreased for the second trial.

Preferentially, the left trial sphere power value and the right trial sphere power value are modified in a symmetrical way by a same amount. For example, when the difference between the left trial sphere power value and the right trial sphere power value is increased by 0.3 D, the higher value between those two is increased by 0.15 D and the lower value between those two is decreased by 0.15 D.

Here, left trial sphere power value and the right trial sphere power value both cannot be lower than a threshold value. This threshold value is for example −0.05 D. For example, when the difference between the left trial sphere power value and the right trial sphere power value must be increased by 0.3 D and when the lower value is equal to 0 D, the lower value is decreased to −0.05 D and the higher value is increased by 0.25 D.

More generally, when the result of a trial is a first answer 110, 221, 211, 231, the test value is increased and when the result of a trial is the second answer 120, 222, 212, 232, the test value is decreased.

If the subject sees the targets as equally sharp in both optical situations S1, S2, the result of the first trial is the third answer 130.

But, as described above, obtaining the third answer as a result of the first trial is regarded as a misunderstanding of the test by the subject. Here, in this case, the second test value V2" is also determined, in step d) referenced 30, as the difference between the first test value V1 and the first variation increment I1, i.e. as if the result of the first trial is the second answer.

As long as the result of the successive test is the third answer 233, the test value is determined as the difference between the previous test value and the previous variation increment, i.e. is decreased.

Preferentially, between the first trial and the last trial of the sequence, the variation increment is preferentially decreased.

Unless the results of all preceding trials are a third answer, when the result is a third answer 213, 223 the intermediary value VI1, VI3 is determined as equal to the last test value V2, V2'. This corresponds to the first stop conditions.

As in the second subjective test, the intermediary value VI2, VI4 is for example determined when the results of two successive trials are a first answer 110, 211, 231 followed by a second answer 212, or conversely, a second answer 120, 222 followed by a first answer 221. In this case, the intermediary value VI2, VI4 is equal to the current test value VC, VC' which is determined as the difference, or respectively the sum, between the previous test value V2, V2' and the previous variation increment I2, I2', where the previous variation increment I2, I2' is equal to half its immediately preceding variation increment I1. This case corresponds to the second stop condition.

Finally, the intermediary value VI5 can also be determined be determined when the results of two successive trials are a third answer 130, 233 followed by a first answer 231. In this case, the intermediary value VI5 is equal to the current test value VC" which is determined as the sum between the previous test value V2" and the previous variation increment I2", where the previous variation increment I2" is equal to half its immediately preceding variation increment I1.

Preferentially, between the first trial and the last trial of the sequence, the variation increment is decreased. Preferentially, it is decreased from one trial to the next. For example, the first variation increment V1 can be superior to 1 D and the second variation V2 inferior to 1 D. Subsequently, the current variation increment can become even lower than the basic dioptric value. The basic dioptric value is for example 0.25 D.

In this fifth sequence, in step f), the rounded value is determined by rounding the intermediary value to the closest or second closest multiple of the basic dioptric value. As described above, the rounding method can depend on a personal feature of the subject.

In a well known manner, sequences relating to different subjective test may be performed in series one after another. For example, a sequence of the fifth subjective test is preferentially performed after performing twice, one the left eye and one the right eye, a sequence of the fourth subjective test.

In the above-described example of subjective tests, the rounded value is determined at the end of the sequence of trials of each subjective test.

When performing series of subjective test, that is to say, several different subjective tests performed successively, determining the rounded values of the optical features looked for may be performed at the end of the sequence of trials of each subjective test or at the end of all the subjective tests.

In this last case, the accurate, non rounded values of the optical features determined through the previously performed subjective tests may be used in the following subjective test. In practice the accurate, non rounded values of the optical features determined through the previously performed subjective tests correspond to the intermediary values described above.

In particular, when determining the cylinder axis power and the cylinder power of a cylinder ophthalmic lens, the intermediary value representative of the cylinder axis is preferentially taken into account when performing the subjective test to determine the cylinder power.

The rounded values of both intermediary values determined through the subjective tests for determining cylinder axis and cylinder power may be rounded after both subjective tests have been performed. In this way, the determination of the intermediary value representative of the cylinder power is more accurate as it takes into account the intermediary value of the cylinder axis and not its rounded value.

In a variant, when performing series of subjective tests, only the last intermediary value determined in the last sequence may be rounded. The preceding series may only serve to determine an accurate first test value.

For example, when only the difference in sphere between right and left eye is looked for, the fifth subjective test is preferentially performed using in step a) the intermediary value determined in a first or fourth subjective tests for the left eye and the intermediary value determined in a first or fifth subjective tests for the left eye.

The invention claimed is:

1. A system for determining a rounded value of an optical feature of at least an ophthalmic lens adapted to provide a dioptric correction for improving vision of a subject, said system including
an optical device for performing a subjective test including assessing visual performance of the subject placed in two different optical situations and a computer comprising at least one processor programmed to:
a) determine a first test value of the optical feature and a first variation increment of the optical feature,
b) perform, using said optical device, a first trial of said subjective test wherein two first different optical situations are determined based on at least the first test value,
c) determine a second test value of the optical feature based on the first test value, on the first variation increment and on the result of the first trial performed in b),
d) perform, using said optical device, a second trial of said subjective test wherein two second different optical situations are determined based on at least the second test value,
e) determine an intermediary value of the optical feature based on a result of the first trial performed in b) and on a result of the second trial performed in d), and
f) determine said rounded value of the optical feature by rounding said intermediary value to a reference value, said rounding modifying the dioptric correction of said ophthalmic lens by less than a predetermined basic dioptric value.

2. The system according to claim 1, wherein the processor is further programmed to round, in f), said intermediary value to the closest or the second closest multiple of said predetermined basic dioptric value, when said intermediary value of the optical feature is different from a multiple value of said predetermined basic dioptric value.

3. The system according to claim 1, wherein the processor is further programmed to, in a), determine the first variation increment based on at least a first personal feature of the subject.

4. The system according to claim 3, wherein the first personal feature comprises at least one of following data relative to the subject: age, type of ametropia, visual acuity, complaints regarding visual performance or current vison correction equipment, historical data including current correction of the subject, pathologies, visual needs or activities, chosen spectacle frame, chosen ophthalmic lens, and optical feature of an eye of the subject.

5. The system according to claim 1, wherein the processor is further programmed to, in f), round said intermediary value according to a rounding approach depending on at least a second personal feature of the subject or depending on the type of subjective test performed.

6. The system according to claim 5, wherein the second personal feature comprises at least one of following data relative to the subject: age, type of ametropia, visual acuity, complaints regarding visual performance or current vison correction equipment, historical data including current correction of the subject, pathologies, visual needs or activities, chosen spectacle frame, chosen ophthalmic lens, and optical feature of an eye of the subject.

7. The system according to claim 1, wherein the processor is further programmed to determine, in b), the two first different optical situations based on the first variation increment.

8. The system according to claim 1, wherein said subject is placed in said two different optical situations during said subjective test by achieving at least one of the following:
displaying targets placed in a red and green environment,
adding, in front of an eye of the subject a cross cylinder in two different positions,
placing, in front of the eye of the subject, two lenses of different spheres,
displaying two targets of different sizes, and
placing different lenses in front of a right and left eye of the subject.

9. The system according to claim 1, wherein the optical feature comprises at least one of following:
sphere power of said ophthalmic lens,
cylinder power of said ophthalmic lens,
cylinder axis of said ophthalmic lens, and
difference in sphere power between two ophthalmic lenses placed in front of right and left eyes.

10. The system according to claim 1, wherein the processor is further programmed to:
g) determine a current test value and a current variation increment based on the result of a preceding trial and on a preceding test value corresponding to said preceding trial,
h) perform a current trial of said subjective test, including assessing the visual performance of the subject placed in two current different optical situations determined based on at least the current test value,
i) modify the current test value based on the result of the current trial and on the current variation increment, and modifying the current variation increment based on the result of the current trial, and,
optionally, repeat h) and i), and
wherein the processor is further programmed to determine, in e), said intermediary value based on the current test.

11. The system according to claim 10, wherein the processor is further programmed to determine, in g), and/or to modify, in i), the current variation increment based on a degree of certainty of the result of the preceding trial performed.

12. The system according to claim 10, wherein the current variation increment is smaller than said predetermined basic dioptric value.

13. The system according to claim 10, wherein the processor is further programmed to modify, in i), the current variation increment by decreasing its value.

14. The system according to claim 10, wherein the processor is further programmed perform e), when:
the current test value is successively increased and decreased or decreased and increased in the last two successive trials, or
the second test value is higher than the first test value and the current test value determined in g) is smaller than the second test value, or
the second test value is smaller than the first test value and the current test value determined in g) is higher than the second test value.

15. The system according to claim 1, wherein the processor is further programmed perform e), when:
during a final trial the subject assesses two final different optical situations to provide an equivalent visual performance, and
during a preceding trial performed before said final trial, the subject assessed one of two different preceding optical situations, to provide a better quality of vision than the other preceding optical situation.

16. A method for determining a rounded value of optical feature of an ophthalmic lens adapted to provide a dioptric correction for improving vision of a subject comprising:
a) determining a first test value of the optical feature and a first variation increment of the optical feature;
b) using an optical device, performing a first trial of a subjective test wherein two first different optical situations are determined based on at least the first test value;
c) determining a second test value of the optical feature based on the first test value, on the first variation increment and on the result of the first trial performed in step b);
d) using said optical device, performing a second trial of said subjective test wherein two second different optical situations are determined based on at least the second test value;
e) determining an intermediary value of the optical feature based on the result of the first trial performed in step b) and on the result of the second trial performed in in step d); and
f) determining said rounded value of the optical feature by rounding said intermediary value to a reference value, said rounding modifying the dioptric correction of said ophthalmic lens by less than a predetermined basic dioptric value.

* * * * *